United States Patent [19]

Kawamatsu et al.

[11] 4,376,777
[45] Mar. 15, 1983

[54] THIAZOLIDINE DERIVATIVES USE

[75] Inventors: Yutaka Kawamatsu, Kyoto; Takashi Sohda, Takatsuki; Takeo Hirata, Osaka, all of Japan

[73] Assignee: Takeda Chemical Industries, Ltd., Osaka, Japan

[21] Appl. No.: 222,881

[22] Filed: Jan. 6, 1981

[30] Foreign Application Priority Data

Jan. 7, 1980 [JP] Japan .................................. 55-762

[51] Int. Cl.³ .................. C07D 277/04; A61K 31/425
[52] U.S. Cl. ...................................... 424/270; 548/183
[58] Field of Search ......................... 548/183; 424/270

[56] References Cited

U.S. PATENT DOCUMENTS

| | | | |
|---|---|---|---|
| 3,200,126 | 8/1965 | Satzinger | 548/183 |
| 3,311,655 | 3/1967 | Boileau et al. | 548/183 |
| 3,825,553 | 7/1974 | Diamond et al. | 548/83 |
| 4,287,200 | 9/1981 | Kawamatsu et al. | 424/270 |

OTHER PUBLICATIONS

Jour. of Medicinal Chemistry 13, 1009–1012, (1970).

*Primary Examiner*—Nicholas S. Rizzo
*Attorney, Agent, or Firm*—Wenderoth, Lind & Ponack

[57] ABSTRACT

A thiazolidine derivative of the formula:

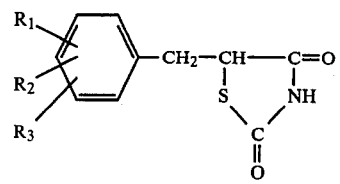

wherein $R_1$ is hydrogen, hydroxyl, lower alkyl having 1 to 4 carbon atoms, lower alkoxy having 1 to 4 carbon atoms, or lower carboxylic acyloxy having 2 to 4 carbon atoms; each of $R_2$ and $R_3$ is hydroxyl, lower alkyl having 1 to 4 carbon atoms, lower alkoxy having 1 to 4 carbon atoms or lower carboxylic acyloxy having 2 to 4 carbon atoms or pharmaceutically acceptable salt thereof a is a novel compound having antiulcer activity and inhibitory effect on gastric acid secretion. The compound is useful as antiulcer agent or inhibitory agent of gastric acid secretion.

19 Claims, No Drawings

THIAZOLIDINE DERIVATIVES USE

This invention relates to a novel thiazolidine derivative having antiulcer activity and inhibitory effect on gastric acid secretion, its production and its use as an antiulcer agent.

More particularly, this invention relates to:

1. A thiazolidine derivative of the formula:

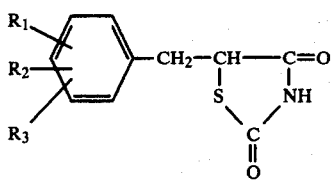

wherein $R_1$ is hydrogen, hydroxyl, lower alkyl having 1 to 4 carbon atoms, lower alkoxy having 1 to 4 carbon atoms or lower carboxylic acyloxy having 2 to 4 carbon atoms; each of $R_2$ and $R_3$ is hydroxyl, lower alkyl having 1 to 4 carbon atoms, lower alkoxy having 1 to 4 carbon atoms or lower carboxylic acyloxy having 2 to 4 carbon atoms or a pharmaceutically acceptable salt thereof.

2. A method of producing a thiazolidine derivative of the formula (I), which comprises reacting an α-halocarboxylic acid compound of the formula:

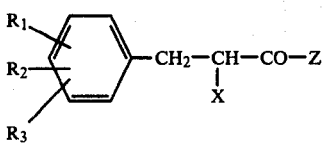

wherein $R_1$, $R_2$ and $R_3$ are as defined above; X is a halogen; Z is a lower alkoxy having 1 to 4 carbon atoms, hydroxyl, amino or a group of the formula OM (wherein M is an alkali metal or ammonium), with thiourea to give a 2-iminothiazolidine derivative of the formula

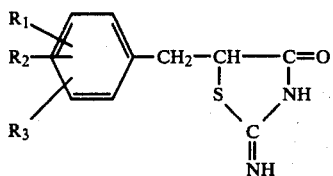

or

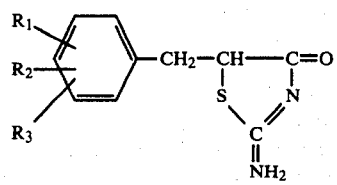

wherein all symbols are as defined above, and then hydrolyzing the 2-iminothiazolidine derivative.

3. A method for treatment of a mammal suffering from an ulcer, which comprises administering to said mammal an effective amount of a thiazolidine derivative of the formula (I) or pharmaceutically acceptable salt thereof.

4. A medicinal composition for the treatment of a mammal suffering from an ulcer, which comprises an effective amount of a thiazolidine derivative of the formula (I) or a pharmaceutically acceptable salt thereof as an active ingredient, and a physiologically acceptable carrier, excipient or diluent therefor.

Referring to the general formulas (I), (II), (III-a) and (III-b), the lower alkyl having 1 to 4 carbon atoms designated by $R_1$, $R_2$ and $R_3$ is a straight-chain or branched alkyl group such as methyl, ethyl, n-propyl, i-propyl, n-butyl, i-butyl and t-butyl. The lower alkoxy having 1 to 4 carbon atoms designated by $R_1$, $R_2$ and $R_3$ is such a group as methoxy, ethoxy, n-propoxy and i-propoxy. The lower carboxylic acyloxy having 2 to 4 carbon atoms designated by $R_1$, $R_2$ and $R_3$ is such an acyloxy group as acetyloxy and propionyloxy. These substituents may be present in optional positions on the benzene ring. In the general formula (II), the halogen designated by X may for example be chlorine or bromine and the lower alkoxy having 1 to 4 carbon atoms designated by Z is such an alkoxy group as methoxy, ethoxy, n-propoxy, i-propoxy, n-butoxy, i-butoxy and t-butoxy. When Z is a group represented by OM, the metal atom M may for example be sodium, potassium or lithium. As the pharmaceutically acceptable salt of the compound (I), there may for example be mentioned sodium salt, potassium salt, calcium salt, etc.

The thiazolidine derivative (I) shows an excellent inhibitory effect on gastric acid secretion and antiulcer activities in mammals (e.g. human being, mouse, rat, rabbit, dog and monkey), and it is used for alleviation or therapy of peptic ulcers (e.g. gastric ulcer, duodenal ulcer, etc.) and gastric juice hypersecretion, etc.

The thiazolidine derivative (I) may be safely administered, orally or parenterally as it is or advantageously as a pharmaceutical composition comprising an effective amount of the compound (I) and a physiologically acceptable carrier, excipient or diluent therefor, in the form of, for example, powder, granule, tablet, hard capsule, soft capsule, dry syrup, suppository, injection or the like.

The composition for oral administration such as powder, granule, tablet, hard capsule, soft capsule and dry syrup may be prepared by a per se known conventional manner, and may comprise carriers, excipients or diluents conventionally used in the pharmaceutical art. For example, suitable carriers or excipients include lactose, starch, sugar, magnesium stearate, etc. As the excipients in the preparation of soft capsules, there may be used nontoxic, pharmaceutically acceptable oils and fats of animal, vegetable or mineral origin. The essential active ingredients are generally dissolved in these oils and fats before filling soft capsules therewith.

The compositions for parenteral administration may, for example, be injections and suppositories. The injectable preparations may be prepared in the form of solutions or suspensions. Since compounds (I) are soluble in oil but only sparingly soluble in water, injectable preparations in the form of aqueous solutions may be prepared by using solubilizing agents, if desired. As such solubilizing agents, there may be used nonionic surfactants that have adequate HLB values and are selected from among the nonionic surfactants generally used in the preparation of injectable solutions. The suppositories for rectal administration can be prepared by incorporating the compound (I) with a conventional suppository base.

The composition of this invention contains a drug of dosage unit form. The drug of dosage unit form means a drug containing a daily dose of the compound (I) to be described hereinafter, or its multiples (up to 4 times), or its measures (down to 1/40), which is in a physically separate unit form suitable for administering as a medicine.

The dosage of the compound (I) varies with the kinds of diseases, symptoms, administration routes or dosage forms, but, in case of oral administration, the daily dose is about 50 mg to 500 mg (1 mg to 10 mg/kg), for adult humans.

In a test in mice (each group consisting of 5 mice), when the compounds (I) of the present invention, for example, 5-(2,4-dimethoxybenzyl)thiazolidine-2,4-dione and 5-(2,4-tripropoxybenzyl)thiazolidine-2,4-dione, were administered at a dose of 2000 mg/kg once, no mouse died.

The thiazolidine derivative (I) can be produced for example by the following procedure. First, an α-halocarboxylic acid compound of the general formula (II) is reacted with thiourea to obtain a 2-iminothiazolidine derivative of general formula (III-a) or (III-b) which is then hydrolyzed. It should be understood that compounds (III-a) and (III-b) are tautomers and herein will sometimes be referred to collectively as compound (III).

The reaction of an α-halocarboxylic acid compound (II) with thiourea is usually conducted in a solvent. The solvent includes, for example, alcohols (e.g. methanol, ethanol, propanol, butanol, ethylene glycol monomethyl ether), ethers (e.g. tetrahydrofuran, dioxane), acetone, dimethylsufoxide, sulfolane and dimethylformamide. The proportions of the reactants are not critical but it is usually recommended to employ equimolar amounts or a slight excess of thiourea to each mole of α-halocarboxylic acid compound (II). A preferred ratio is 1 to 2 moles per mole of (II). The reaction conditions such as temperature and time depend on the starting compound, solvent and other factors but usually the reaction is conducted at the boiling temperature of the solvent or at a temperature between 100° and 130° C. for a few to 10 or more hours. The reaction gives the imino-derivative (III) which is sparingly soluble. This step is followed by a hydrolysis procedure, with or without interposition of a step of isolating the imino-derivative (III).

The hydrolysis reaction of imino-derivative (III) is carried out at an elevated temperature in a suitable solvent (e.g. sulfolane) and in the presence of water and mineral acid. The amount of acid is usually 0.1 to 10 moles and preferably 0.2 to 3 moles to each mole of α-halocarboxylic acid compound (II). The amount of water is usually a large excess over α-halocarboxylic acid (II). The heating time is usually a few to ten or more hours.

The thiazolidine derivative (I) thus produced can be isolated and purified by conventional procedures such as concentration at atmospheric or reduced pressure, solvent extraction, crystallization, recrystallization, phasic transfer and chromatography.

The α-halocarboxylic acid (II), which is the starting material used in the production of compound (I), can be produced, for example, by diazotizing the corresponding phenylamine compound and subjecting diazo compound to Meerwein arylation. Alternatively, the following routes of synthesis can also be employed.

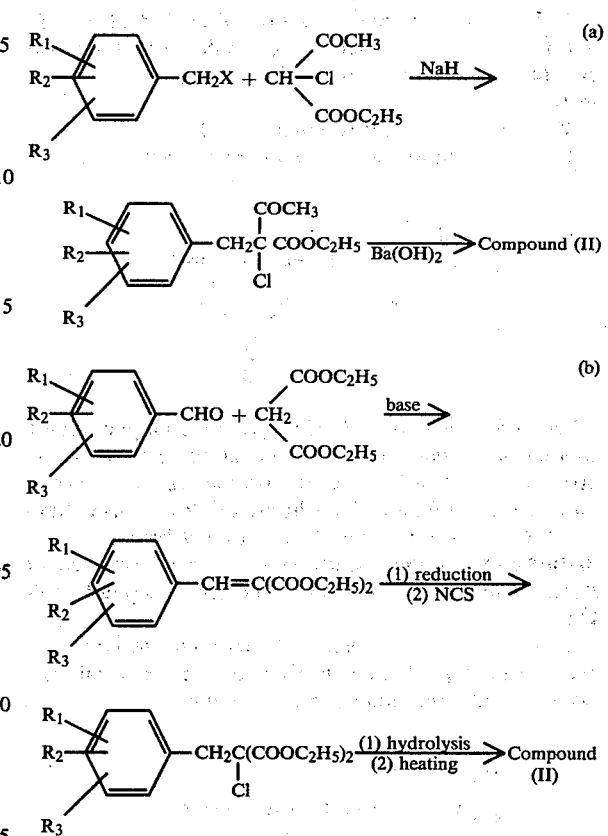

The following reference examples, experimental data and working examples are given to further illustrate this invention.

REFERENCE EXAMPLE 1

In 100 ml of dry dimethylformamide is dissolved 9.6 g of ethyl 2-chloroacetoacetate, and under ice cooling, 2.32 g of 60% sodium hydride in oil is added. The mixture is stirred at room temperature for 30 minutes. To this mixture are added 12.5 g of 3,4-diethoxybenzyl chloride and 30 ml of dry dimethylformamide, and the mixture is stirred at 70° C. for 2 hours. The mixture is then poured into a mixture of 200 g ice and 50 ml 6N-HCl and extracted with ether. The ethereal layer is washed with water, dried over MgSO$_4$ and distilled to remove the ether. Column chromatography is carried out on the oily residue with 200 g of silica gel, elution being carried out with a 1:4 mixture of ether and n-hexane. The above procedure provides 14.2 g (71.4%) of ethyl 2-acetyl-2-chloro-3-(3,4-diethoxyphenyl)propionate as oil.

In 150 ml of ethanol is dissolved 14.0 g of the above ethyl 2-acetyl-2-chloro-3-(3,4-diethoxyphenyl)propionate, followed by addition of 3.5 g of anhydrous barium hydroxide. The mixture is stirred under ice cooling for 30 minutes, then poured into 300 g ice-40 ml 6N-HCl, and extracted with ether. The ethereal layer is washed with water, dried (over MgSO$_4$) and distilled to remove the ether. The above procedure provides 12.0 g (97.6%) of ethyl 2-chloro-3-(3,4-diethoxyphenyl)propionate as oil.

REFERENCE EXAMPLE 2

In 80 ml of acetone is dissolved 12.1 g of 3,4-xylidine, followed by addition of 25 ml of concentrated HCl. Then, a solution of 7.6 g of sodium nitrite in 25 ml of water is added at a temperature not above 5° C. and the mixture is stirred at that temperature for 15 minutes. After addition of 63 ml of methyl acrylate, 0.5 g of cuprous oxide is added in small portions and the mixture is vigorously stirred, whereupon nitrogen gas is evolved to increase the temperature of the reaction system to 45° C. After the evolution of nitrogen gas has subsided, the solvent is distilled off under reduced pressure and the residue is extracted with ethyl acetate. The organic layer is washed with water, dried (over MgSO$_4$) and distilled to remove the solvent. The procedure provides 21.9 g (96.5%) of a crude oil of methyl 2-chloro-3-(3,4-dimethylphenyl)propionate.

REFERENCE EXAMPLE 3

In 80 ml of toluene is dissolved 5.9 g of 2,4,5-trimethoxybenzaldehyde, followed by addition of 4.8 g of diethyl malonate, 0.3 ml of piperidine and 0.3 g of benzoic acid. The mixture is heated under reflux for 4 hours, water being removed via an ester tube. After cooling, the solvent is distilled off under reduced pressure and the residual crystals are recovered by filtration with n-hexane to give 8.9 g (87.3%) of diethyl 2,4,5-trimethoxybenzylidenemalonate, m.p. 86°-87° C.

In 100 ml of methanol is dissolved 8.5 g of the diethyl 2,4,5-trimethoxybenzylidenemalonate obtained above, and in the presence of 1 g of 10% palladium-on-carbon (50% wet), catalytic reduction is carried out at room temperature and atmospheric pressure. In about 30 minutes, about 0.6 l of hydrogen is absorbed. The palladium-on-carbon is filtered off and the solvent is distilled off under reduced pressure to give 7.0 g of diethyl 2,4,5-trimethoxybenzylmalonate as crystals melting at 50°-51° C.

In 70 ml of anhydrous tetrahydrofuran is dissolved 6.5 g of diethyl 2,4,5-trimethoxybenzylmalonate and, then, 760 mg of 60% oily sodium hydride is added. The mixture is stirred at room temperature for 15 minutes, after which time 2.54 g of N-chlorosuccinimide is added. The mixture is further stirred at room temperature for 30 minutes. The reaction mixture is poured into a mixture of 300 ml water and 10 ml 6N-HCl and, then, extracted with ether. The ethereal layer is washed with water, dried (over MgSO$_4$) and distilled to remove the ether, whereupon 6.5 g (91.5%) of diethyl α-chloro-α-(2,4,5-trimethoxybenzyl)malonate is obtained as crystals melting at 84°-85° C.

In 60 ml of methanol is dissolved 6.0 g of the above diethyl α-chloro-α-(2,4,5-trimethoxybenzyl)malonate, and after addition of 2N-KOH, the solution is stirred at room temperature for 1 hour. The solution is then made acidic with 6N-HCl and extracted with ethyl acetate. The extract is washed with water, dried (over MgSO$_4$) and distilled to remove the solvent. The oily residue is dissolved in 60 ml of acetic acid and heated under reflux for 2 hours. The reaction solution is cooled and subjected to distillation under reduced pressure to remove the acetic acid to give 4.2 g of an oily substance which is a mixture of 2-chloro-3-(2,4,5-trimethoxyphenyl)propionic acid and its ethyl ester.

EXAMPLE 1

Ethyl 2-chloro-3-(3,4-dimethoxyphenyl)propionate (5.8 g) and thiourea (3.2 g) are stirred in sulfolane (60 ml) at 120° C. for 20 hours, and 20 ml of 1N-HCl is added thereto. The mixture is stirred at 100° C. for 6 hours. After cooling the mixture, water is added thereto and extraction is carried out with ether. The extract is washed with water, dried (over Na$_2$SO$_4$) and distilled to remove the ether, whereby 4.5 g (80.4%) crystals of 5-(3,4-dimethoxybenzyl)thiazolidine-2,4-dione are obtained Recrystallization from methanol gives colorless prisms melting at 162°-163° C.

EXAMPLE 2

In 120 ml of ethylene glycol monomethyl ether is dissolved 11.7 g of ethyl 2-chloro-3-(3,4-diethoxyphenyl)propionate, followed by addition of 4.4 g of thiourea and 3.8 g of sodium acetate. The mixture is stirred at 110° C. for 15 hours. The solvent is distilled off under reduced pressure, water is added to the residue and extraction is carried out with ethyl acetate. The extract is washed with water, dried (over MgSO$_4$) and distilled to remove the ethyl acetate. The above procedure provides 7.5 g (65.2%) of 5-(3,4-diethoxybenzyl)-2-iminothiazolidin-4-one as crystals melting at 171°-172° C.

In a mixture of 60 ml ethanol and 60 ml 1N-HCl is dissolved 5.0 g of the 5-(3,4-diethoxybenzyl)-2-iminothiazolidin-4-one prepared above and the solution is heated under reflux for 8 hours. The reaction solution is cooled, and water is added thereto. The aqueous mixture is subjected to extraction with chloroform to give 4.3 g (86.0%) of 5-(3,4-diethoxybenzyl)thiazolidine-2,4-dione as crystals. Recrystallization from ethyl acetate-n-hexane yields colorless prisms melting at 98°-99° C.

EXAMPLE 3

The compounds listed in Table 1 were prepared by procedures similar to Example 1 or 2.

TABLE 1

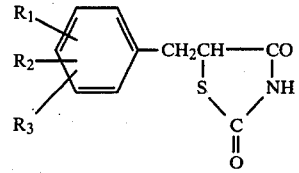

| No. | R$_1$ | R$_2$ | R$_3$ | m.p. (°C.) | Recrystallization solvent | Corresponding Example No. |
|---|---|---|---|---|---|---|
| 1 | 5-OCH$_3$ | 2-OCH$_3$ | 4-OCH$_3$ | 141–142 | Ethyl acetate-n-hexane | 2 |
| 2 | 5-OC$_2$H$_5$ | 2-OC$_2$H$_5$ | 4-OC$_2$H$_5$ | 104–105 | Ethyl acetate-n-hexane | 1 |
| 3 | 5-OC$_3$H$_7$ | 2-OC$_3$H$_7$ | 4-OC$_3$H$_7$ | 87–88 | Cyclohexane | 2 |
| 4 | 5-OCH$_3$ | 3-OCH$_3$ | 4-OCH$_3$ | 157–158 | Ethyl acetate-n-hexane | 2 |
| 5 | H | 3-OC$_2$H$_5$ | 4-OCOCH$_3$ | 113–114 | Ethyl acetate-n-hexane | 2 |
| 6 | H | 3-OH | 4-OH | 168–169 | Ethyl acetate | 1 |
| 7 | H | 3-CH$_3$ | 4-CH$_3$ | 119– | Methanol | 1 |

TABLE 1-continued

R1, R2, R3 substituted benzyl-CH2CH(S)-CO-NH-C(=O) thiazolidine structure

| No. | R1 | R2 | R3 | m.p. (°C.) | Recrystal- lization solvent | Corre- spond- ing Exam- ple No. |
|---|---|---|---|---|---|---|
| 8 | H | 2-OCH3 | 4-OCH3 | 120 171–172 | Ethanol | 1 |
| 9 | H | 2-OH | 3-OCH3 | 137–138 | Ethyl acetate-n-hexane | 2 |
| 10 | H | 3-OC2H5 | 5-OC2H5 | 121–122 | Ethanol-water | 2 |
| 11 | H | 3-OCH3 | 5-OCH3 | 110–111 | Ethyl acetate-n-hexane | 1 |
| 12 | H | 2-OCH3 | 3-OCH3 | 112–113 | Ethyl acetate-n-hexane | 1 |

EXPERIMENT 1

The compounds according to this invention were subjected to the following biological tests. The results are summarized in Table 2.

1. Pyloric ligation assay (3 hrs., Shay's method)*1

Male rats of the SD strain (7 weeks old, body weights 190–240 g) were fasted for 24 hours. Water was made available ad libitum.

Under light ether anesthesia, a midline abdominal incision was made and the pylorus was ligated. After 3 hours, the gastric juice accumulated in the stomach was collected and centrifuged at 8000 r.p.m. for 10 minutes. The volume of the supernatant fluid was measured and a portion of the fluid was taken to determine its acidity ($\mu$Eq/ml). The acidity determination was carried out by neutralizing titration with 1/50 N-NaOH in an automatic titrator.

Each test compound was suspended in 5% gum arabic solution and administered intraduodenally at the time of pyloric ligation. (Dose: 50 mg/kg). The inhibitory action of each compound was analyzed by Student's t-test and expressed as % change using an untreated group (given 5% gum arabic only) as control.

2. Water-immersion stress ulceration assay*2

Male rats of the SD strain (7 weeks old, body weights 190–240 g) were fasted for 24 hours (with free access to water) before the assay was performed. The rats were housed in the compartments of a stainless-steel stress cage and immersed in a water bath controlled at 23° C. down to the xiphoid. After 5 hours, the stomach was enuclerated under ether anesthesia and with the esophagus clipped, 10 ml of 1% formalin was introduced from the duodenum into the stomach. The stomach was then kept immersed in 1% formalin for 10 minutes. The stomach was incised along the greater curvature and the gastric mucosa was examined for ulcerative lesions under an optical microscope (magnification: X10). The major diameter (mm) of each lesion was measured, the lengths of all lesion are totalled and the sum was taken as the ulcer index for the case.

Each test compound was suspended in 5% gum arabic and administered orally 30 minutes before water immersion (Dose: 50 mg/kg). The effect of each test compound was analyzed by Student's t-test and expressed as % change using an untreated group (5% gum arabic only) as control.

Literature

*1: Shay, H. et al: A simple method for the uniform production of gastric ulceration in the rat. Gastroenterology, 5, 43, (1945).
*2: Takagi, K. and Okabe, S.: The effects of drugs on the production and recovery process of the stress ulcer. Jap. J. Pharmac., 18, 9, (1968).

TABLE 2

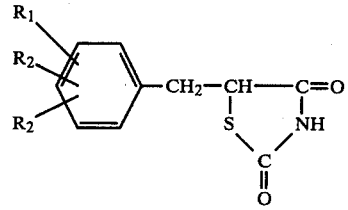

| No. | R1 | R2 | R3 | Antiulcer action[1] | Inhibition of gastric secretion[2] |
|---|---|---|---|---|---|
| 1 | 5-OCH3 | 2-OCH3 | 4-OCH3 | 92*** | 81** |
| 2 | 5-OC2H5 | 2-OC2H5 | 4-OC2H5 | 85* | 19 |
| 3 | 5-OC3H7 | 2-OC3H7 | 4-OC3H7 | 70** | 63* |
| 4 | 5-OCH3 | 3-OCH3 | 4-OCH3 | 90** | 50* |
| 5 | H | 3-OCH3 | 4-OCH3 | 76* | 38* |
| 6 | H | 3-OC2H5 | 4-OC2H5 | 67** | 22 |
| 7 | H | 3-OC2H5 | 4-OCOCH3 | 62** | 24 |
| 8 | H | 3-OH | 4-OH | 63** | 35 |
| 9 | H | 3-CH3 | 4-CH3 | 53** | 23 |
| 10 | H | 2-OCH3 | 4-OCH3 | 61* | — |
| 11 | H | 2-OH | 3-OCH3 | 45* | — |
| 12 | H | 3-OC2H5 | 5-OC2H5 | 50 | 41 |

*$P < 0.05$,
**$P < 0.01$,
***$P < 0.001$

EXAMPLE 4

A typical formulation for the compound of this invention as an antiulcer drug.

(Tablet)

| | | |
|---|---|---|
| (1) | 5-(2,4,5-Tripropoxybenzyl)-thiazolidine-2,4-dione | 10 mg |
| (2) | Lactose | 35 mg |
| (3) | Corn starch | 170 mg |
| (4) | Microcrystalline cellulose | 30 mg |
| (5) | Magnesium stearate | 5 mg |
| | | 250 mg (per tablet) |

The components (1), (2), and (3) and ⅔ of the component (4) are admixed and granulated. To the granules is added the remaining ⅓ of (4) and (5), and the mixture is molded into a tablet. The tablet is coated with a suitable coating material.

(Capsules)

| | |
|---|---|
| 5-(2,4-Dimethoxybenzyl)thiazolidine-2,4-dione | 10 mg |
| Microcrystalline cellulose | 30 mg |
| Lactose | 57 mg |
| Magnesium stearate | 3 mg |

-continued

| | |
|---|---|
| | 100 mg |

The above ingredients are mixed in a conventional manner and gelatin capsules are filled with the mixture to prepare capsules.

(Tablet)

| 5-(2,4-Dimethoxybenzyl)thiazolidine-2,4-dione | 20 mg |
|---|---|
| Lactose | 44 mg |
| Starch | 10.6 mg |
| Starch (for making paste) | 5 mg |
| Magnesium stearate | 0.4 mg |
| Carboxymethylcellulose calcium | 20 mg |
| | 100 mg |

The above ingredients are mixed and made into tablets in a conventional manner.

(Injectable solution)

In 2 g of Nikkol HCO-120 ® (Polyoxyethylene hydrogenated ricinolate; Produced by Nikko Chemicals, Japan) is dissolved with warming 0.2 g of 5-(3,4-dimethoxybenzyl)thiazolidine-2,4-dione. To the solution are added 0.4 g of monosodium phosphate and 0.1 g of disodium phosphate to make the pH about 6. There are further added 0.9 g of sodium chloride and 1 g of benzyl alcohol, and then distilled water is added to make the whole volume 100 ml. The mixture is placed in containers, followed by sealing and heat sterilization to prepare an injectable solution.

(Soft capsule)

| 5-(2,4,5-Tripropoxybenzyl)thiazolidine-2,4-dione | 30 mg |
|---|---|
| Corn oil | 110 mg |
| | 140 mg |

The above ingredients are mixed to make a solution and then soft capsules are filled with the solution in a conventional manner.

What is claimed is:

1. A thiazolidine compound of the formula:

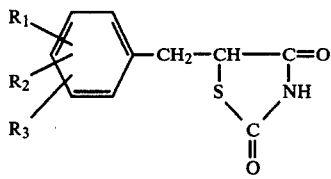

wherein
R₁ is hydrogen, hydroxyl, alkyl having 1 to 4 carbon atoms, alkoxy having 1 to 4 carbon atoms, or carboxylic acyloxy having 2 to 4 carbon atoms, and
each of R₂ and R₃ is hydroxyl, alkyl having 1 to 4 carbon atoms, alkoxy having 1 to 4 carbon atoms, or carboxylic acyloxy having 2 to 4 carbon atoms, or a pharmaceutically acceptable salt thereof.

2. A thiazolidine compound as claimed in claim 1, wherein R₁ is hydrogen and each of R₂ and R₃ is alkoxy having 1 to 4 carbon atoms.

3. A thiazolidine compound as claimed in claim 1, wherein each of R₁, R₂ and R₃ is alkoxy having 1 to 4 carbon atoms.

4. A thiazolidine compound as claimed in claim 1, wherein the compound is 5-(2,4-dimethoxybenzyl)-thiazolidine-2,4-dione.

5. A thiazolidine compound as claimed in claim 1, wherein the compound is 5-(2,4,5-tripropoxybenzyl)-thiazolidine-2,4-dione.

6. A thiazolidine compound as claimed in claim 1, wherein the compound is 5-(3,4-dimethoxybenzyl)-thiazolidine-2,4-dione.

7. A thiazolidine compound as claimed in claim 1, wherein the compound is 5-(3,4-diethoxybenzyl)-thiazolidine-2,4-dione.

8. A thiazolidine compound as claimed in claim 1, wherein the compound is 5-(2,4,5-trimethoxybenzyl)-thiazolidine-2,4-dione.

9. A thiazolidine compound as claimed in claim 1, wherein the compound is 5-(2,4,5-triethoxybenzyl)-thiazolidine-2,4-dione.

10. A thiazolidine compound as claimed in claim 1, wherein the compound is 5-(3,4,5-trimethoxybenzyl)-thiazolidine-2,4-dione.

11. A thiazolidine compound as claimed in claim 1, wherein the compound is 5-(3-ethoxy-4-acetoxybenzyl)thiazolidine-2,4-dione.

12. A thiazolidine compound as claimed in claim 1, wherein the compound is 5-(3,4-dihydroxybenzyl)-thiazolidine-2,4-dione.

13. A thiazolidine compound as claimed in claim 1, wherein the compound is 5-(3,4-dimethylbenzyl)-thiazolidine-2,4-dione.

14. A thiazolidine compound as claimed in claim 1, wherein the compound is 5-(2-hydroxy-3-methoxybenzyl)thiazolidine-2,4-dione.

15. A thiazolidine compound as claimed in claim 1, wherein the compound is 5-(3,5-diethoxybenzyl)-thiazolidine-2,4-dione.

16. A thiazolidine compound as claimed in claim 1, wherein the compound is 5-(3,5-dimethoxybenzyl)-thiazolidine-2,4-dione.

17. A thiazolidine compound as claimed in claim 1, wherein the compound is 5-(2,3-dimethoxybenzyl)-thiazolidine-2,4-dione.

18. A method for treatment of a mammal suffering from an ulcer, which comprises administering to said mammal an effective amount of a thiazolidine compound of the formula:

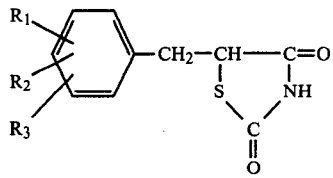

wherein
R₁ is hydrogen, hydroxyl, alkyl having 1 to 4 carbon atoms, alkoxy having 1 to 4 carbon atoms, or carboxylic acyloxy having 2 to 4 carbon atoms, and
each of R₂ and R₃ is hydroxyl, alkyl having 1 to 4 carbon atoms, alkoxy having 1 to 4 carbon atoms, or carboxylic acyloxy having 2 to 4 carbon atoms, or a pharmaceutically acceptable salt thereof.

19. A medicinal composition for the treatment of a mammal suffering from an ulcer, which comprises:
(A) as an active ingredient, an effective amount of a thiazolidine compound of the formula:

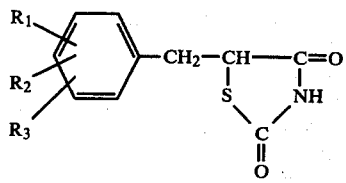

wherein
R$_1$ is hydrogen, hydroxy, alkyl having 1 to 4 carbon atoms, alkoxy having 1 to 4 carbon atoms, or carboxylic acyloxy having 2 to 4 carbon atoms, and
each of R$_2$ and R$_3$ is hydroxyl, alkyl having 1 to 4 carbon atoms, alkoxy having 1 to 4 carbon atoms, or carboxylic acyloxy having 2 to 4 carbon atoms,
or a pharmaceutically acceptable salt thereof, and
(B) a physiologically acceptable carrier, excipient or diluent therefor.

* * * * *